United States Patent
Kirschman

(10) Patent No.: US 10,327,910 B2
(45) Date of Patent: Jun. 25, 2019

(54) SPINAL IMPLANT AND ASSEMBLY

(71) Applicant: X-spine Systems, Inc., Miamisburg, OH (US)

(72) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 402 days.

(21) Appl. No.: 13/804,972

(22) Filed: Mar. 14, 2013

(65) Prior Publication Data

US 2014/0277456 A1    Sep. 18, 2014

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2002/30004* (2013.01); *A61F 2002/30014* (2013.01); *A61F 2002/30131* (2013.01); *A61F 2002/30383* (2013.01); *A61F 2002/30492* (2013.01); *A61F 2002/30604* (2013.01); *A61F 2002/30787* (2013.01); *A61F 2002/30904* (2013.01); *A61F 2002/4475* (2013.01)

(58) Field of Classification Search
CPC .................. A61F 2/4405; A61F 2/4455; A61F 2002/443; A61F 2/447
USPC ................................................. 606/289, 290
See application file for complete search history.

(56) References Cited

U.S. PATENT DOCUMENTS

| | | |
|---|---|---|
| 2,677,369 A | 5/1954 | Knowles |
| 3,228,393 A | 1/1966 | Michele |
| 3,426,364 A | 2/1969 | Lumb |
| 3,848,601 A | 11/1974 | Ma et al. |
| 3,867,728 A | 2/1975 | Stubstad et al. |
| D245,259 S | 8/1977 | Shen |
| 4,309,777 A | 1/1982 | Patil |
| 4,349,921 A | 9/1982 | Kuntz |
| 4,501,269 A | 2/1985 | Bagby |
| 4,554,914 A | 11/1985 | Kapp et al. |
| 4,714,469 A | 12/1987 | Kenna |
| 4,743,256 A | 5/1988 | Brantigan |
| 4,759,769 A | 7/1988 | Hedman et al. |
| 4,820,305 A | 4/1989 | Harms |
| 4,834,757 A | 5/1989 | Brantigan |
| 4,863,477 A | 9/1989 | Monson |
| 4,878,915 A | 11/1989 | Brantigan |
| 4,904,261 A | 2/1990 | Dove et al. |
| 4,932,969 A | 6/1990 | Frey et al. |
| 4,946,378 A | 8/1990 | Hirayama et al. |

(Continued)

FOREIGN PATENT DOCUMENTS

| | | |
|---|---|---|
| WO | 2006101837 | 9/2006 |
| WO | 2010054181 | 5/2010 |

*Primary Examiner* — Anu Ramana
(74) *Attorney, Agent, or Firm* — Sheridan Ross P.C.

(57) ABSTRACT

An implant assembly is shown and described. The implant has at least one or a plurality of elastic, resilient or flexible arms that each have a detent adapted to retain at least one screw in a locked position in the implant. At least one of the arms has a portion that extends into a screw aperture such that an arm axis is generally parallel to the axis of the screw after the screw is received in the implant. In another embodiment, means or a system for locking the multi-component implant members together is shown.

62 Claims, 8 Drawing Sheets

(56) References Cited

U.S. PATENT DOCUMENTS

| | | |
|---|---|---|
| 4,955,908 A | 9/1990 | Frey |
| 4,961,740 A | 10/1990 | Ray |
| 4,963,152 A | 10/1990 | Hofmann |
| 5,011,484 A | 4/1991 | Breard |
| 5,015,247 A | 5/1991 | Michelson |
| 5,015,248 A | 5/1991 | Burstein et al. |
| 5,062,850 A | 11/1991 | MacMillan |
| 5,071,437 A | 12/1991 | Steffee |
| 5,108,438 A | 4/1992 | Stone |
| 5,122,130 A | 6/1992 | Keller |
| 5,123,926 A | 6/1992 | Pisharodi |
| 5,147,402 A | 9/1992 | Bohler |
| 5,171,278 A | 12/1992 | Pisharodi |
| 5,171,281 A | 12/1992 | Parsons et al. |
| 5,192,327 A | 3/1993 | Brantigan |
| 5,258,031 A | 11/1993 | Salib |
| 5,261,911 A | 11/1993 | Carl |
| 5,282,861 A | 2/1994 | Kaplan |
| 5,306,308 A | 4/1994 | Gross et al. |
| 5,306,309 A | 4/1994 | Wagner et al. |
| 5,320,644 A | 6/1994 | Baumgartner |
| 5,344,459 A | 9/1994 | Swartz |
| 5,360,430 A | 11/1994 | Lin |
| 5,370,697 A | 12/1994 | Baumgartner |
| 5,397,364 A | 3/1995 | Kozak |
| 5,423,825 A | 6/1995 | Lavine |
| 5,423,826 A | 6/1995 | Coates et al. |
| 5,425,772 A | 6/1995 | Brantigan |
| 5,443,514 A | 8/1995 | Steffee |
| 5,458,638 A | 10/1995 | Kuslich et al. |
| 5,458,642 A | 10/1995 | Beer |
| 5,458,643 A | 10/1995 | Oka et al. |
| 5,514,180 A | 5/1996 | Heggeness |
| 5,520,690 A | 5/1996 | Errico et al. |
| 5,522,899 A | 6/1996 | Michelson |
| 5,527,312 A | 6/1996 | Ray |
| 5,534,028 A | 7/1996 | Bao |
| 5,534,030 A | 7/1996 | Navarro et al. |
| 5,545,229 A | 8/1996 | Parsons et al. |
| 5,554,191 A | 9/1996 | Lahille |
| 5,578,034 A | 11/1996 | Estes |
| 5,593,409 A | 1/1997 | Michelson |
| 5,599,279 A | 2/1997 | Slotman et al. |
| 5,609,637 A | 3/1997 | Biedermann et al. |
| 5,653,761 A | 8/1997 | Pisharodi |
| 5,658,337 A | 8/1997 | Kohrs et al. |
| 5,676,702 A | 10/1997 | Ratron |
| 5,702,449 A | 12/1997 | McKay |
| 5,702,450 A | 12/1997 | Bisserie |
| 5,713,899 A | 2/1998 | Marnay et al. |
| 5,716,415 A | 2/1998 | Steffee |
| 5,722,977 A | 3/1998 | Wilhelmy |
| 5,728,159 A | 3/1998 | Stroever et al. |
| 5,755,798 A | 5/1998 | Papavero et al. |
| 5,766,252 A | 6/1998 | Henry et al. |
| 5,776,196 A | 7/1998 | Matsuzaki et al. |
| 5,776,199 A | 7/1998 | Michelson |
| 5,782,919 A | 7/1998 | Zdeblick et al. |
| 5,824,094 A | 10/1998 | Serhan et al. |
| 5,861,041 A | 1/1999 | Tienboon |
| 5,865,845 A | 2/1999 | Thalgott |
| 5,868,745 A | 2/1999 | Alleyne |
| 5,876,457 A | 3/1999 | Picha et al. |
| 5,888,224 A | 3/1999 | Beckers et al. |
| 5,888,226 A | 3/1999 | Rogozinski |
| 5,888,227 A | 3/1999 | Cottle |
| 5,897,556 A | 4/1999 | Drewry et al. |
| 5,989,289 A | 11/1999 | Coates et al. |
| 6,022,376 A | 2/2000 | Assell et al. |
| 6,030,390 A | 2/2000 | Mehdizadeh |
| 6,039,761 A | 3/2000 | Li et al. |
| 6,042,582 A | 3/2000 | Ray |
| 6,045,580 A | 4/2000 | Scarborough et al. |
| 6,059,829 A | 5/2000 | Schlapfer et al. |
| 6,063,088 A | 5/2000 | Winslow |
| 6,066,174 A | 5/2000 | Farris |
| 6,066,175 A | 5/2000 | Henderson et al. |
| 6,074,390 A | 6/2000 | Zucherman et al. |
| 6,080,158 A | 6/2000 | Lin |
| 6,083,225 A | 7/2000 | Winslow et al. |
| 6,093,205 A | 7/2000 | McLeod et al. |
| 6,093,207 A | 7/2000 | Pisharodi |
| 6,096,038 A | 8/2000 | Michelson |
| 6,099,527 A | 8/2000 | Hocschuler et al. |
| 6,113,602 A | 9/2000 | Sand |
| 6,132,464 A | 10/2000 | Martin |
| 6,132,465 A | 10/2000 | Ray et al. |
| 6,136,002 A | 10/2000 | Shih et al. |
| 6,139,551 A | 10/2000 | Michelson et al. |
| 6,139,579 A | 10/2000 | Steffee et al. |
| 6,143,031 A | 11/2000 | Knothe et al. |
| 6,146,422 A | 11/2000 | Lawson |
| 6,156,037 A | 12/2000 | LeHuec et al. |
| 6,156,067 A | 12/2000 | Bryan et al. |
| 6,159,215 A | 12/2000 | Urbahns et al. |
| 6,159,244 A | 12/2000 | Suddaby |
| 6,159,245 A | 12/2000 | Meriwether et al. |
| 6,174,311 B1 | 1/2001 | Branch et al. |
| 6,210,412 B1 | 4/2001 | Michelson |
| 6,224,602 B1 | 5/2001 | Hayes |
| 6,224,607 B1 | 5/2001 | Michelson |
| 6,231,610 B1 | 5/2001 | Geisler |
| 6,235,059 B1 | 5/2001 | Benezech et al. |
| 6,245,108 B1 | 6/2001 | Biscup |
| 6,258,089 B1 | 7/2001 | Campbell et al. |
| 6,261,296 B1 | 7/2001 | Aebi et al. |
| 6,261,586 B1 | 7/2001 | McKay |
| 6,264,655 B1 | 7/2001 | Pisharodi |
| 6,267,763 B1 | 7/2001 | Castro |
| 6,270,498 B1 | 8/2001 | Michelson |
| 6,277,149 B1 | 8/2001 | Boyle et al. |
| 6,302,914 B1 | 10/2001 | Michelson |
| 6,306,136 B1 | 10/2001 | Baccelli |
| 6,315,797 B1 | 11/2001 | Middleton |
| 6,319,257 B1 | 11/2001 | Carignan et al. |
| 6,328,738 B1 | 12/2001 | Suddaby |
| 6,387,130 B1 | 5/2002 | Stone et al. |
| 6,402,756 B1 | 6/2002 | Ralph et al. |
| 6,402,785 B1 | 6/2002 | Zdeblick et al. |
| 6,432,106 B1 | 8/2002 | Fraser |
| 6,478,796 B2 | 11/2002 | Zucherman et al. |
| 6,478,800 B1 | 11/2002 | Fraser et al. |
| 6,576,017 B2 | 6/2003 | Foley et al. |
| 6,579,318 B2 | 6/2003 | Varga et al. |
| 6,592,586 B1 | 7/2003 | Michelson |
| 6,610,065 B1 | 8/2003 | Branch et al. |
| 6,635,087 B2 | 10/2003 | Angelucci et al. |
| 6,652,533 B2 | 11/2003 | O'Neil |
| 6,666,866 B2 | 12/2003 | Martz et al. |
| 6,770,074 B2 | 8/2004 | Michelson |
| 6,896,676 B2 | 5/2005 | Zubok et al. |
| 6,926,737 B2 | 8/2005 | Jackson |
| 6,972,019 B2 | 12/2005 | Michelson |
| 6,991,654 B2 | 1/2006 | Foley |
| 7,112,222 B2 | 9/2006 | Fraser et al. |
| 7,160,300 B2 | 1/2007 | Jackson |
| 7,163,561 B2 | 1/2007 | Michelson |
| 7,172,627 B2 | 2/2007 | Fiere et al. |
| 7,182,782 B2 | 2/2007 | Kirschman |
| 7,232,464 B2 | 6/2007 | Mathieu |
| 7,235,105 B2 | 6/2007 | Jackson |
| 7,244,258 B2 | 7/2007 | Burkus et al. |
| 7,250,052 B2 | 7/2007 | Landry et al. |
| 7,252,673 B2 | 8/2007 | Lim |
| 7,300,441 B2 | 11/2007 | Haid et al. |
| 7,435,261 B1 | 10/2008 | Castro |
| 7,537,603 B2 | 5/2009 | Huebner et al. |
| 7,547,306 B2 | 6/2009 | Michelson |
| 7,594,931 B2 | 9/2009 | Louis et al. |
| D603,503 S | 11/2009 | Kriska et al. |
| 7,618,456 B2 | 11/2009 | Mathieu et al. |
| 7,621,938 B2 | 11/2009 | Molz, IV |
| 7,628,816 B2 | 12/2009 | Magerl et al. |
| 7,637,911 B2 | 12/2009 | Zubok et al. |

(56) References Cited

U.S. PATENT DOCUMENTS

| | | |
|---|---|---|
| 7,637,952 B2 | 12/2009 | Landry et al. |
| 7,641,665 B2 | 1/2010 | Zubok et al. |
| 7,641,701 B2 | 1/2010 | Kirschman |
| 7,648,511 B2 | 1/2010 | Zubok et al. |
| 7,655,028 B2 | 2/2010 | Kirschman |
| 7,674,292 B2 | 3/2010 | Zubok et al. |
| 7,704,250 B2 | 4/2010 | Michelson |
| 7,726,002 B2 | 6/2010 | Shimp et al. |
| 7,740,630 B2 | 6/2010 | Michelson |
| 7,749,269 B2 | 7/2010 | Peterman et al. |
| 7,758,616 B2 | 7/2010 | LeHuec et al. |
| 7,815,681 B2 | 10/2010 | Ferguson |
| 7,862,616 B2 | 1/2011 | Lechmann et al. |
| 7,972,363 B2 | 7/2011 | Moskowitz et al. |
| 8,062,367 B2 | 11/2011 | Kirschman |
| 8,097,037 B2 | 1/2012 | Serhan et al. |
| 8,100,955 B2 | 1/2012 | Blain et al. |
| 8,187,329 B2 * | 5/2012 | Theofilos ............ 623/17.11 |
| 8,187,334 B2 | 5/2012 | Curran et al. |
| 8,206,449 B2 | 6/2012 | Jansen et al. |
| 8,216,312 B2 | 7/2012 | Gray |
| 8,216,316 B2 | 7/2012 | Kirschman |
| 8,262,697 B2 | 9/2012 | Kirschman |
| 8,282,682 B2 | 10/2012 | Kirschman |
| 8,372,152 B2 | 2/2013 | Kirschman |
| 8,439,953 B2 | 5/2013 | Mitchell et al. |
| 8,454,694 B2 | 6/2013 | Armstrong et al. |
| 8,470,039 B2 | 6/2013 | Blain |
| 8,480,747 B2 | 7/2013 | Melkent et al. |
| 8,491,658 B1 | 7/2013 | Etminan |
| 8,496,691 B2 | 7/2013 | Blain |
| 8,496,708 B2 | 7/2013 | Blain |
| 8,500,811 B2 | 8/2013 | Blain et al. |
| 8,696,721 B2 | 4/2014 | Blain |
| 8,945,227 B2 | 2/2015 | Kirschman |
| 2003/0028249 A1 | 2/2003 | Baccelli et al. |
| 2003/0109928 A1 | 6/2003 | Pasquet et al. |
| 2003/0109929 A1 | 6/2003 | Keller |
| 2003/0125739 A1 | 7/2003 | Bagga et al. |
| 2004/0092929 A1 | 5/2004 | Zindrick |
| 2004/0193269 A1 | 9/2004 | Fraser et al. |
| 2005/0065606 A1 | 3/2005 | Jackson |
| 2005/0071008 A1 | 3/2005 | Kirschman |
| 2005/0071013 A1 | 3/2005 | Zubok et al. |
| 2005/0085913 A1 | 4/2005 | Fraser et al. |
| 2005/0096657 A1 | 5/2005 | Autericque et al. |
| 2005/0101960 A1 | 5/2005 | Fiere et al. |
| 2005/0107880 A1 | 5/2005 | Shimp et al. |
| 2005/0149193 A1 | 7/2005 | Zucherman et al. |
| 2005/0159813 A1 | 7/2005 | Molz, IV |
| 2005/0277930 A1 | 12/2005 | Parsons et al. |
| 2005/0288788 A1 | 12/2005 | Dougherty-Shah |
| 2006/0036250 A1 | 2/2006 | Lange et al. |
| 2006/0079961 A1 | 4/2006 | Michelson |
| 2006/0106387 A1 | 5/2006 | Fanger et al. |
| 2006/0116766 A1 | 6/2006 | Lemaire |
| 2006/0149284 A1 | 7/2006 | McCormack et al. |
| 2006/0195100 A1 | 8/2006 | Kirschman |
| 2006/0212120 A1 | 9/2006 | McGahan et al. |
| 2006/0217806 A1 | 9/2006 | Peterman et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235412 A1 | 10/2006 | Blain |
| 2006/0235518 A1 | 10/2006 | Blain |
| 2006/0235533 A1 | 10/2006 | Blain |
| 2006/0265065 A1 | 11/2006 | Bagga et al. |
| 2006/0282165 A1 | 12/2006 | Pisharodi |
| 2007/0010885 A1 | 1/2007 | Liu et al. |
| 2007/0032873 A1 | 2/2007 | Pisharodi |
| 2007/0055252 A1 | 3/2007 | Blain et al. |
| 2007/0123884 A1 | 5/2007 | Abdou |
| 2007/0123885 A1 | 5/2007 | Kirschman |
| 2007/0198016 A1 | 8/2007 | Zang et al. |
| 2007/0270965 A1 | 11/2007 | Ferguson |
| 2008/0021476 A1 | 1/2008 | Kirschman |
| 2008/0154375 A1 | 6/2008 | Serhan et al. |
| 2008/0161925 A1 | 7/2008 | Brittan et al. |
| 2008/0172128 A1 | 7/2008 | Perez-Gruet et al. |
| 2008/0177307 A1 * | 7/2008 | Moskowitz et al. .......... 606/246 |
| 2008/0221694 A1 | 9/2008 | Warnick et al. |
| 2008/0221695 A1 | 9/2008 | Jacofsky et al. |
| 2008/0269806 A1 | 10/2008 | Zhang et al. |
| 2008/0294260 A1 | 11/2008 | Gray |
| 2008/0294262 A1 | 11/2008 | Levieux |
| 2008/0312742 A1 | 12/2008 | Abernathie |
| 2009/0012529 A1 | 1/2009 | Blain et al. |
| 2009/0182428 A1 | 7/2009 | McClellan et al. |
| 2009/0182430 A1 | 7/2009 | Tyber et al. |
| 2009/0198339 A1 | 8/2009 | Kleiner et al. |
| 2009/0228110 A1 | 9/2009 | McClintock |
| 2009/0270927 A1 | 10/2009 | Perrow et al. |
| 2009/0306779 A1 | 12/2009 | Ahn |
| 2009/0306780 A1 | 12/2009 | Bernard et al. |
| 2009/0318977 A1 | 12/2009 | Di Giacomo et al. |
| 2009/0326580 A1 | 12/2009 | Anderson et al. |
| 2010/0049323 A1 | 2/2010 | Gill et al. |
| 2010/0070037 A1 | 3/2010 | Parry et al. |
| 2010/0100131 A1 | 4/2010 | Wallenstein |
| 2010/0100186 A1 | 4/2010 | Zubok et al. |
| 2010/0145453 A1 | 6/2010 | Kirschman |
| 2010/0145459 A1 | 6/2010 | McDonough et al. |
| 2010/0145460 A1 | 6/2010 | McDonough et al. |
| 2010/0152853 A1 | 6/2010 | Krischman |
| 2010/0168798 A1 | 7/2010 | Clineff et al. |
| 2010/0249935 A1 | 9/2010 | Slivka et al. |
| 2010/0249937 A1 | 9/2010 | Blain et al. |
| 2010/0286784 A1 | 11/2010 | Curran et al. |
| 2010/0305701 A1 | 12/2010 | Castro |
| 2010/0324679 A1 | 12/2010 | Castro |
| 2010/0324681 A1 | 12/2010 | Castro |
| 2010/0324682 A1 | 12/2010 | Castro |
| 2011/0046736 A1 | 2/2011 | Graf |
| 2011/0054616 A1 | 3/2011 | Kamran et al. |
| 2011/0060415 A1 | 3/2011 | Bertholet et al. |
| 2011/0082550 A1 | 4/2011 | Yeh |
| 2011/0112587 A1 | 5/2011 | Patel et al. |
| 2011/0172775 A1 | 7/2011 | Flickinger et al. |
| 2012/0010714 A1 | 1/2012 | Moskowitz et al. |
| 2012/0035657 A1 | 2/2012 | Kirschman |
| 2012/0158056 A1 | 6/2012 | Blain |
| 2012/0197399 A1 | 8/2012 | Kirschman |
| 2012/0239151 A1 | 9/2012 | Ulrich et al. |
| 2012/0277868 A1 | 11/2012 | Walters |
| 2012/0277870 A1 | 11/2012 | Wolters et al. |
| 2012/0290091 A1 | 11/2012 | Kirschman |
| 2012/0303126 A1 | 11/2012 | Kirschman |
| 2013/0023940 A1 * | 1/2013 | Hansell et al. ............... 606/289 |
| 2013/0023992 A1 | 1/2013 | Moskowitz et al. |
| 2013/0030530 A1 | 1/2013 | Blain |
| 2013/0197588 A1 * | 8/2013 | Abdou ........................ 606/279 |
| 2013/0253590 A1 | 9/2013 | Blain |
| 2013/0253655 A1 | 9/2013 | Blain |
| 2013/0268008 A1 | 10/2013 | McDonough et al. |
| 2014/0046448 A1 * | 2/2014 | Kana et al. ............... 623/17.16 |
| 2014/0052260 A1 | 2/2014 | McKenny et al. |

* cited by examiner

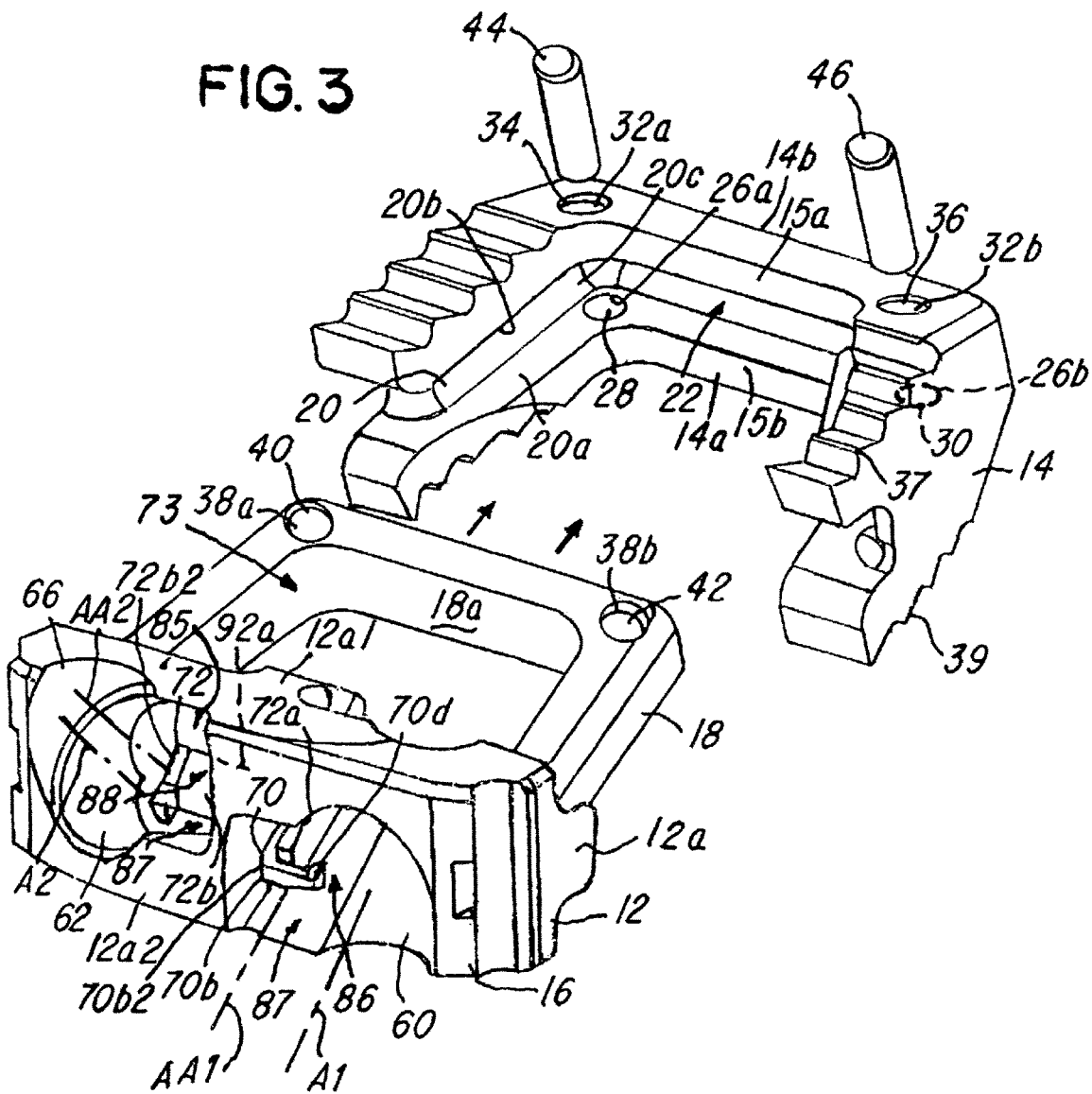

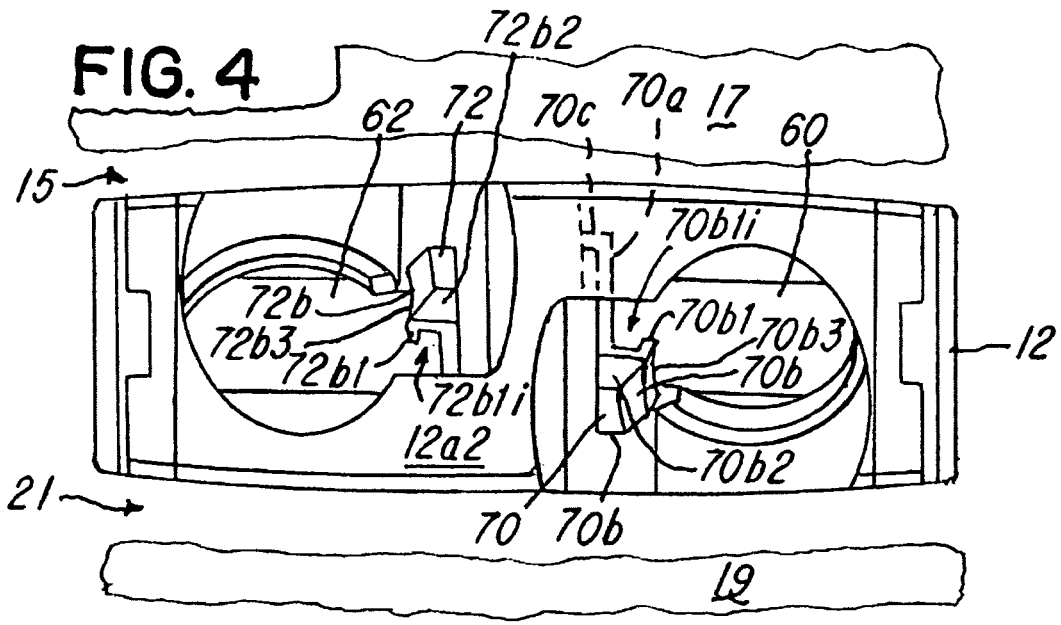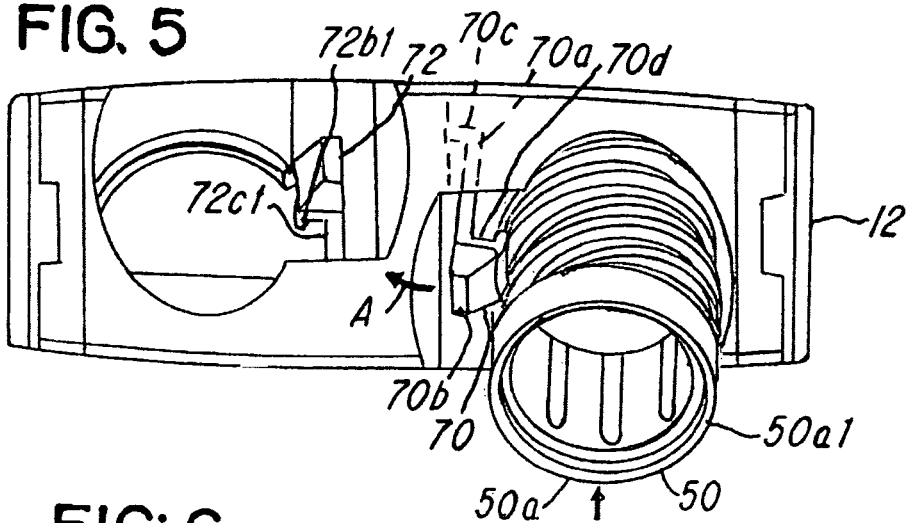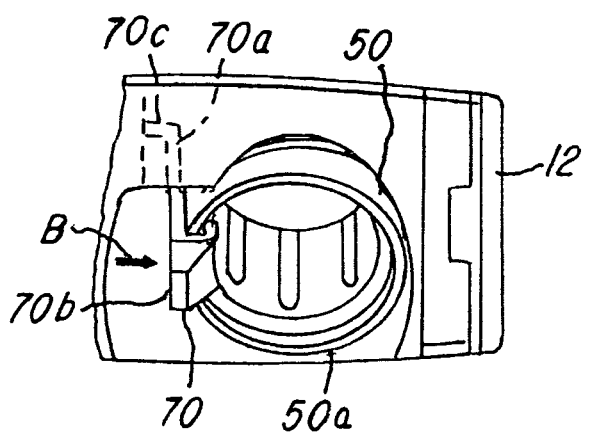

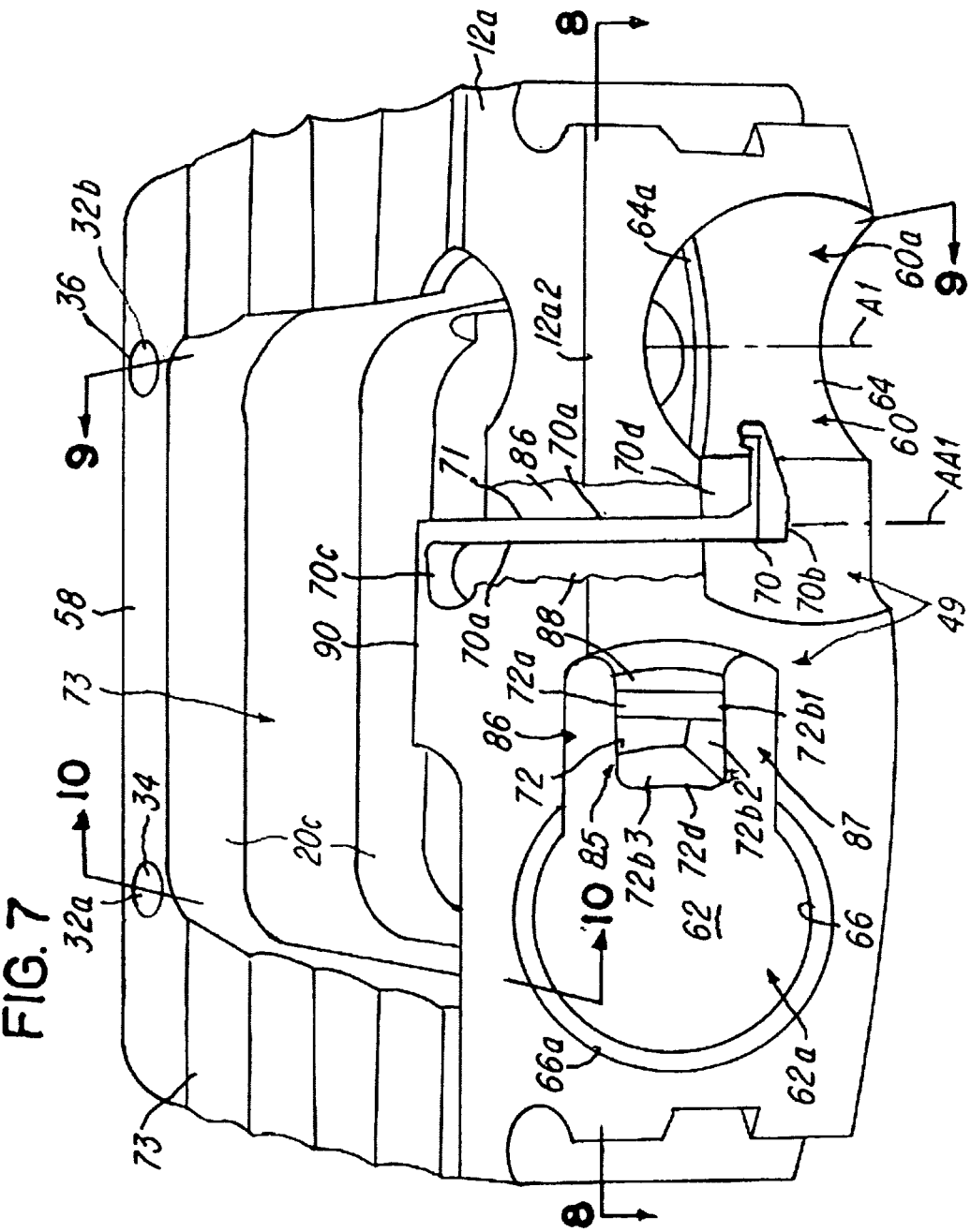

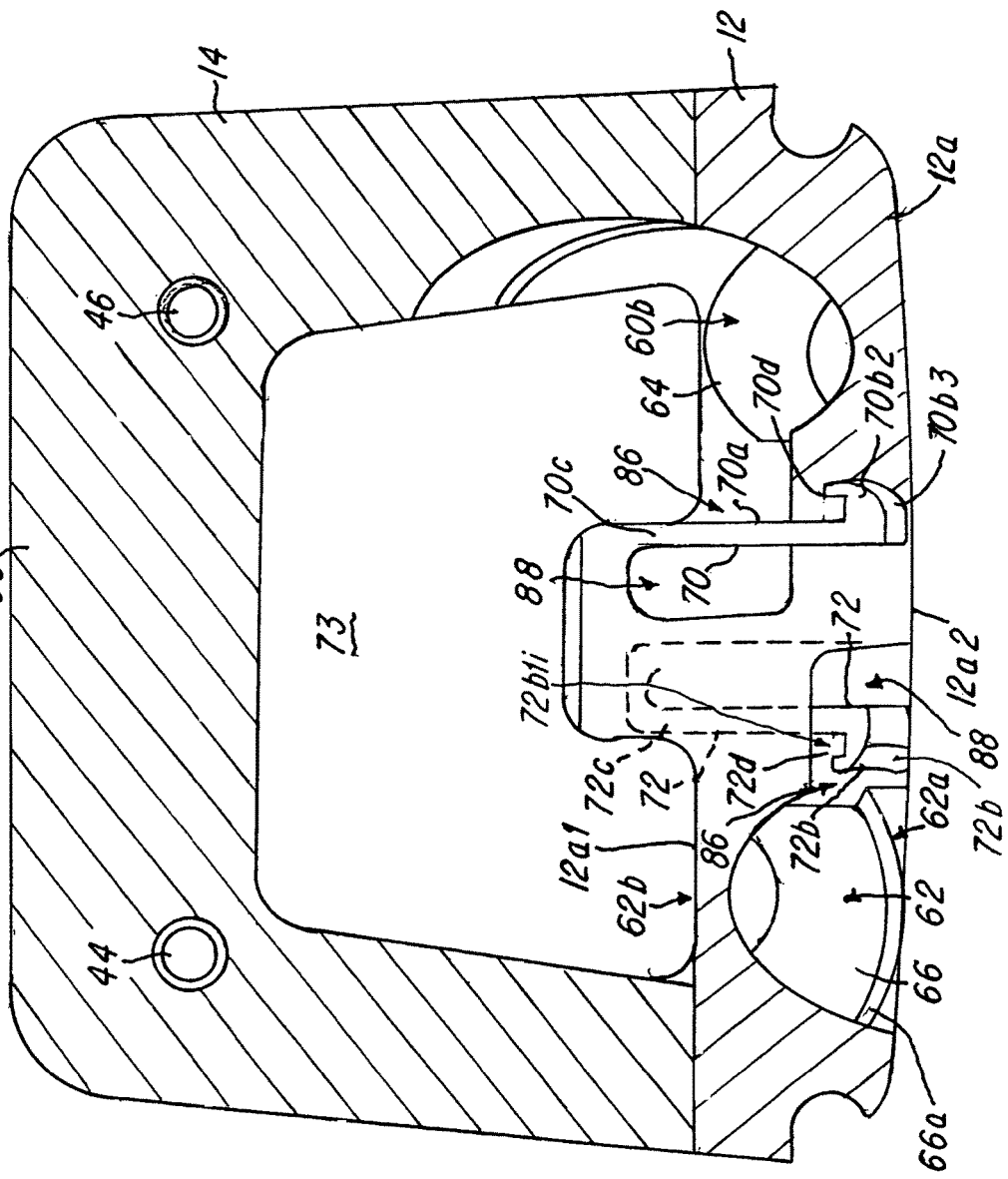

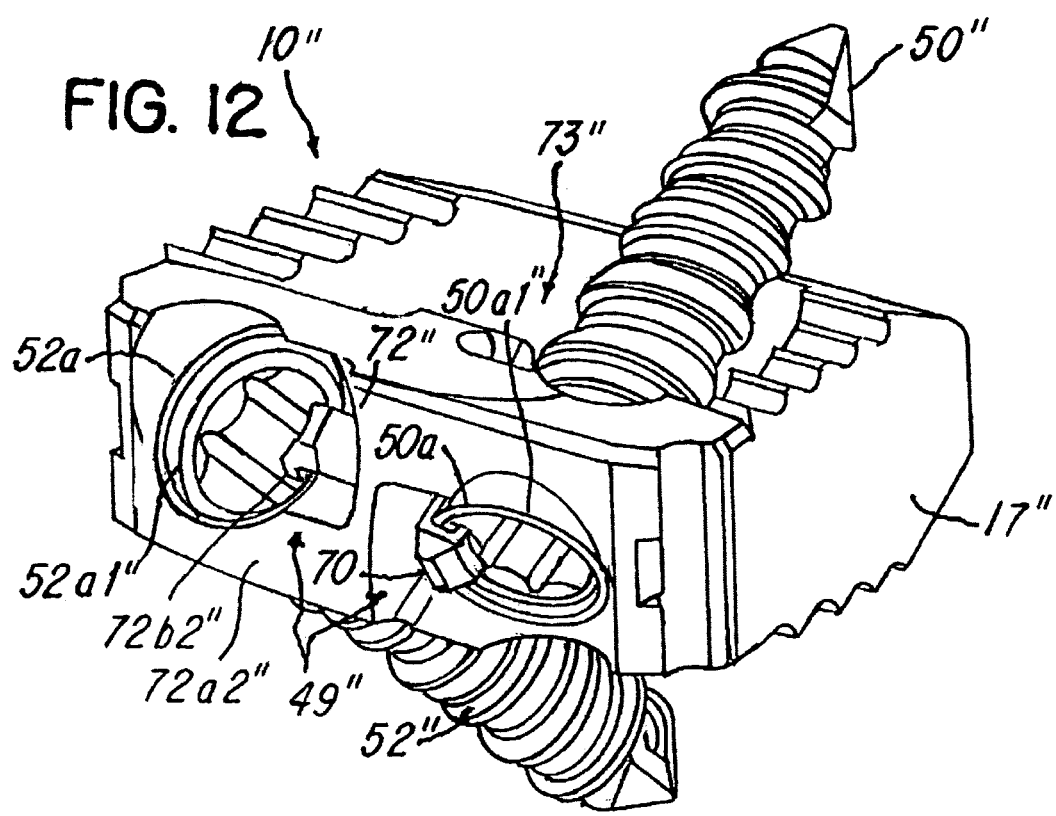

SPINAL IMPLANT AND ASSEMBLY

BACKGROUND OF THE INVENTION

1. Field of the Invention

This invention relates to spinal implants, and more specifically, the invention relates to an implant having at least one resilient, elastic or flexible arm adapted to have an arm axis that becomes generally parallel to an axis of a screw that is received in the implant.

2. Description of the Related Art

Many types of prosthetic devices have been proposed in the past. For example, U.S. Pat. No. 5,192,327 to Brantagan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 5,192,327; 5,261,911; 5,713,899; 5,776,196; 6,136,002; 6,159,245; 6,224,602; 6,258,089; 6,261,586; 6,264,655; 6,306,136; 6,328,738; 6,592,586; 7,182,782 and 7,641,701. Some or all of these devices have improved the success rate and have simplified the surgical techniques in inter-body veritable fusion.

Among some of the problems associated with the prior art devices is that after the device is inserted into a patient during a surgical procedure, there was a possibility of retropulsion of the inter-body device and graft material into the spinal cord or other neurological element.

Another problem with the prior art devices is that grafting material, which was inserted into the devices during the surgical procedure, could not easily be inserted from an anterior direction.

Another problem with some prior art systems is that the screws or fasteners which secured implant to bone sometimes had a tendency to unscrew themselves because the implant itself may move or withdraw.

In some prior art implants, screws are placed at an angle relative to the plane in which the cage lies so that the screws can be screwed directly into an upper vertebra and/or a lower vertebra. While solutions for retaining screws in the implant plates have included, for example, the use of a resilient arm and approaches used in U.S. Pat. No. 7,641,701, these approaches do not work as effectively with implants that use angled screws. Such approaches are also not practical for use with implants that do not have available space for using an arm.

What is needed, therefore, is a screw retaining system that is particularly adapted for use with implants having angled screws. What is also needed is a system and means for locking a multi-component implant assembly together.

SUMMARY OF THE INVENTION

It is, therefore, an object of one embodiment to provide means and a system for locking screws in an implant when there is limited space on the implant for providing an integral lock, for example, or when a face of the implant is narrow.

Another object of one embodiment is to provide a system and means for locking a multi-component implant assembly together.

Still another object of another embodiment is to provide an implant having at least one or a plurality of arms that are used to retain a screw in a locked position in the implant and that facilitate preventing the screws from withdrawing from the implant and from bone.

Still another object of another embodiment is to provide an implant having at least one or a plurality of resilient, elastic or flexible arms having detents, wherein the at least one or a plurality of arms is/are situated in one or more screw apertures of the implant.

Yet another object of one embodiment is to provide an implant having a plurality of flexible, resilient or elastic arms, each having a locking detent, that are adapted to be arranged in a plurality of apertures that are adapted to receive at least one of the arms that has at least one screw and wherein at least one elongated portion is generally parallel to an axis of the screw after the screw is inserted in the implant and screwed into bone.

In one aspect, one embodiment of the invention comprises an implant comprising an implant member adapted to be received in an implant receiving area between a first bone and a second bone comprising at least one aperture adapted to receive a screw having a screw head, the implant member comprising at least one arm having a detent that becomes associated with the screw head after the screw is received in the at least one aperture, the detent being adapted to retain the screw in the at least one aperture and the at least one arm being flexible, resilient or elastic and having a generally elongated portion having an arm axis that is not parallel relative to an imaginary implant plane lying generally midway between a first bone-engaging surface adapted to engage or become associated with the first bone and a second bone-engaging surface, the generally elongated portion extending in the at least one aperture.

In another aspect, another embodiment of the invention comprises an implant assembly comprising an implant member having an imaginary implant plane, the implant member comprising a plurality of apertures each adapted to receive a screw having a screw head, and a second implant member adapted to be received between bones and having an open end configured to mate with the implant member, the implant member comprising a plurality of arms associated with the plurality of apertures, respectively, in the implant member, the plurality of arms being adapted to retain a plurality of screws in the plurality of apertures, respectively, after the plurality of screws have been received in the plurality of apertures, each of the plurality of arms further comprising a generally elongated arm having an elongated arm axis that is not parallel to the imaginary implant plane, the plurality of arms being flexible, resilient or elastic and having a generally elongated portion having an arm axis that is not parallel relative to the imaginary implant plane lying generally midway between a first bone-engaging surface adapted to engage or become associated with a first bone and a second bone-engaging surface, the generally elongated portion extending in the plurality of apertures.

In another aspect, another embodiment of the invention comprises an implant that comprises an implant body having at least one aperture adapted to receive a screw having a locking wall, at least one resilient, elastic or flexible arm adapted to capture at least a portion of the locking wall, thereby locking or retaining said screw in the implant.

Still another object is to provide a resilient, elastic or flexible arm having a U-shaped detent adapted to receive a wall of a screw head.

Another object is to provide a screw locking approach that is adapted to enable a resilient arm to be used on an implant where space on an exterior surface or wall of the implant is constrained.

These and other objects and advantages of the invention will be apparent from the following description, the accompanying drawings and the appended claims.

BRIEF DESCRIPTION OF THE DRAWINGS

FIG. 3 is an exploded view of the implant shown in FIG. 1;

FIG. 4 is a front view of the implant shown in FIG. 1 situated between adjacent vertebrae;

FIG. 5 is another view illustrating a screw causing at least one arm to move to an open position in response to the axial movement of the screw in the implant;

FIG. 6 is a fragmentary view illustrating an arm moving from an open position shown in FIG. 5 to a closed position after a detent "clears" a screw shoulder;

FIG. 6A is a fragmentary view showing features of the detent capturing at the screw wall;

FIG. 7 is an enlarged fragmentary view showing various features of one arm associated with a first aperture;

FIG. 8 is a sectional view taken along the line 8-8 in FIG. 7;

FIG. 12 is a perspective view of an implant that is an integral one-piece construction.

DETAILED DESCRIPTION OF PREFERRED EMBODIMENTS

Figure 1:
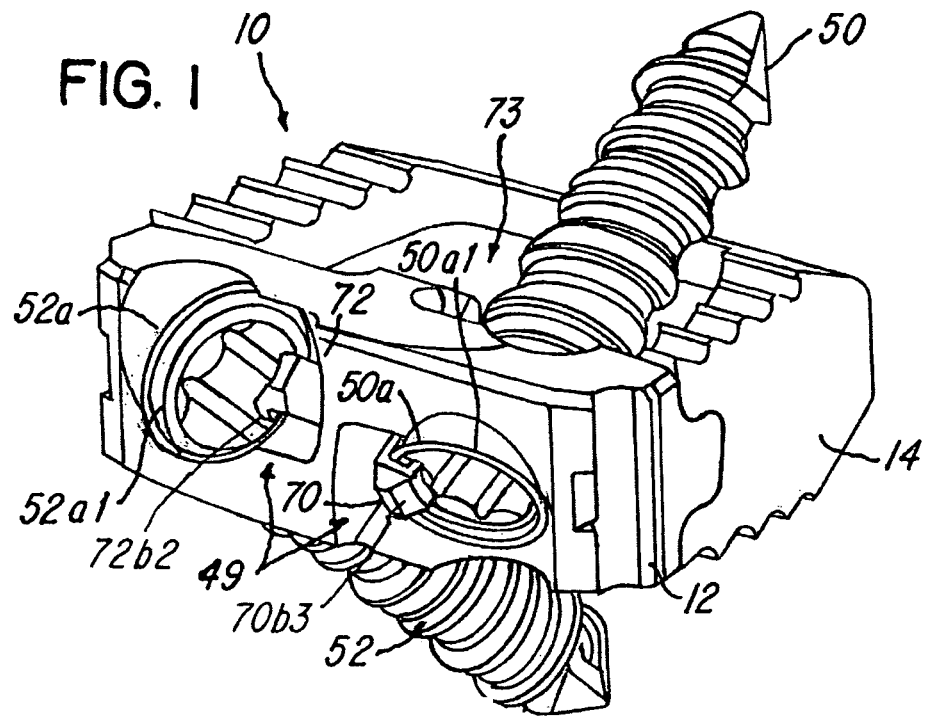
FIG. 1 is a perspective view of an implant in accordance with one embodiment of the invention.

Referring now to FIGS. 1-12, an implant and an implant assembly 10 are shown. The implant assembly 10 comprises a first implant member 12 and a second implant member 14. The implant assembly 10 is adapted to be received in an implant assembly receiving area 15 (FIG. 4) between bones, such as between a first vertebra or bone 17 and a second vertebra or bone 19. The second implant member 14 has an open-end configuration as illustrated in FIG. 3. Further details of the second implant member 14 will be described later herein. Although not shown, it should be understood that the first implant member 12 could have an open-end configuration with U-shaped channel (not shown) and the second implant member 14 could have a mating U-shaped projection (not shown) for receipt in the U-shaped channel.

The first implant member 12 comprises a first wall 16 having a generally U-shaped projection 18. As best illustrated in FIG. 3, note that the second implant member 14 comprises a generally U-shaped wall 20 having a first wall portion 20a, a second wall portion 20b and a third wall portion 20c joining the first and second wall portions 20a, 20b to define a generally U-shaped channel 22. In the illustration being described, the generally U-shaped channel 22 is adapted to provide a guide channel for receiving and guiding the generally U-shaped projection 18, as best illustrated in FIGS. 1 and 3, into a mating or assembled configuration. The generally U-shaped projection 18 is adapted and configured so that it complements the shape of the generally U-shaped channel 22 and fits snugly therein.

As best illustrated in FIG. 3, note that the first wall portion 20a comprises through-holes or bores 28 and 30 defined by generally cylindrical walls 26a and 26b, respectively. Likewise, the second wall portion 20b comprises through-holes or bores 34 and 36 that are defined by generally cylindrical walls 32a and 32b, respectively. Note that the through-holes and bores 34 and 36 are generally aligned with the through-holes or bores 28 and 30, respectively, as shown.

Figure 9:
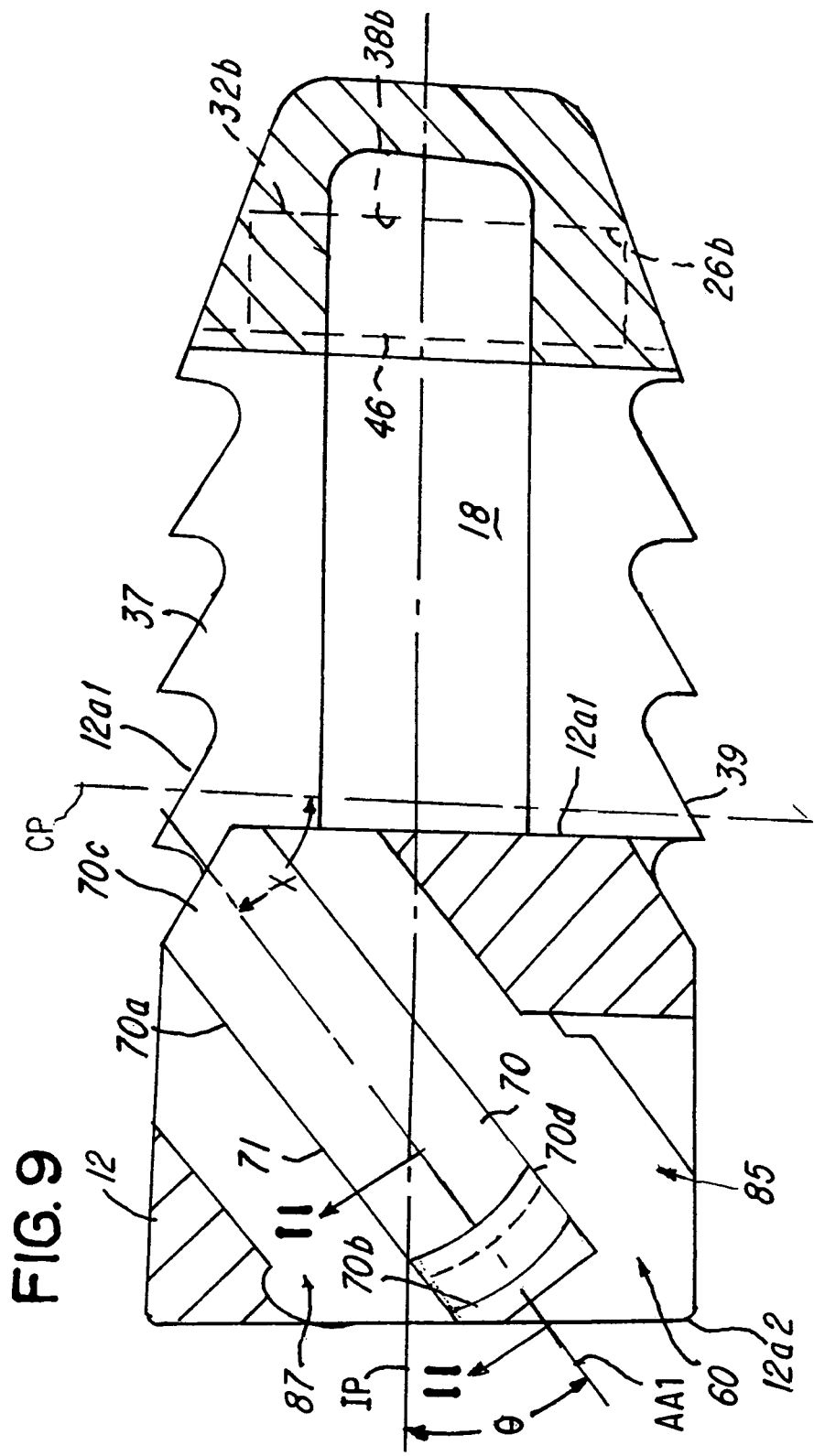
FIG. 9 is a sectional view taken along the line 9-9 in FIG. 7.
Figures 10, 11:
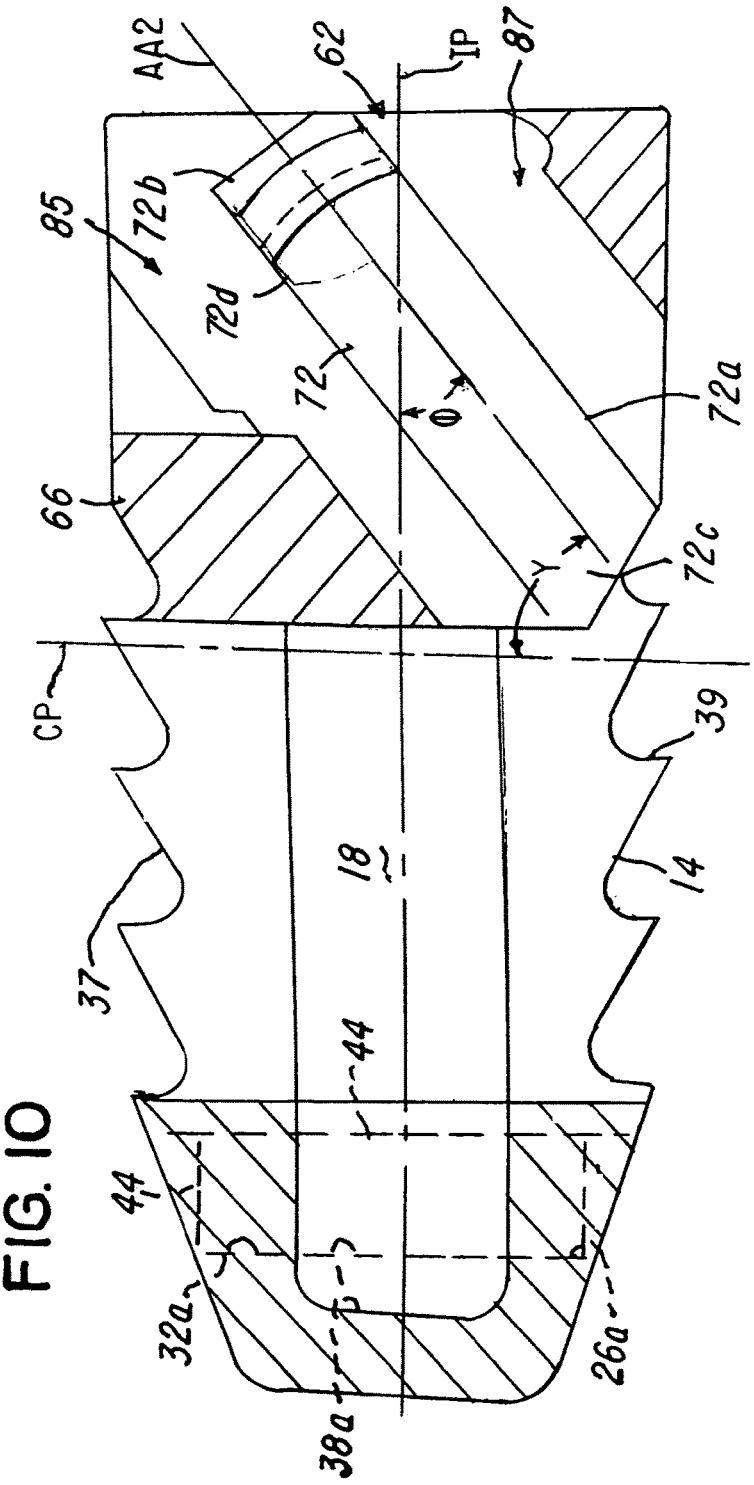
FIG. 10 is a sectional view taken along the line 10-10 in FIG. 7.
FIG. 11 is a perspective view of another embodiment showing an integral one-piece construction.

The generally U-shaped projection 18 likewise comprises a pair of generally cylindrical walls 38a and 38b that define through-holes or bores 40 and 42, respectively. It should be understood that after the first implant member 12 is mounted in the second implant member 14, the through-holes or bores 30, 42 and 36 become generally aligned to provide a first lock aperture and through-holes or bores 28, 40 and 34 being generally aligned to provide a second lock aperture. The first and second lock apertures are adapted to receive pins 44 and 46, respectively, in order to lock the first and second implant members 12 and 14 together. Thus, the implant assembly 10 provides means and apparatus for locking the first and second implant members 12 and 14 together as shown in FIGS. 8-10.

Referring now to FIGS. 3 and 7-10, details of a screw locking system 49 (FIG. 1) will now be described. The screw locking system 49 is adapted to retain at least one or a plurality of screws, such as screws 50 and 52 (FIG. 1), in the implant assembly 10 and prevent them from withdrawing therefrom after the implant assembly 10 is assembled together and implanted in the implant assembly receiving area 15 and the at least one or a plurality of screws 50 and 52 are screwed into the first and second vertebrae or bones 17 and 19, respectively.

The first implant member 12 comprises a first wall 12a, which is anterior or downward of a rear wall 14a of the second implant member 14 after the implant assembly 10 is assembled and implanted. It should be understood that when the implant assembly 10 is inserted into the implant assembly receiving area 15 between the first vertebra or bone 17 and the second vertebra or bone 19 (FIG. 4), the first wall 12a becomes associated with an anterior opening or area 21 into the implant receiving area 15. A second wall or rear wall 14b of the second implant member 14 becomes associated with a posterior area (not shown) of the implant assembly receiving area 15. In general, the first wall 12a is adapted and configured to receive the at least one or a plurality of screws 50 and 52 and the screw locking system 49 secures them in a locked position so that after the at least one or a plurality of screws 50 and 52 are screwed into bone, they will become locked in the implant assembly 10 and not withdraw therefrom. The screw locking system 49, in turn, facilitates preventing the screws 50 and 52 from unscrewing from the bones into which they are screwed.

The first wall 12a comprises at least one or a plurality of apertures or bores, such as bore or aperture 60 (FIG. 3) having a first aperture or bore axis A1 and a second aperture 62 having a second aperture or bore axis A2, respectively. The cylindrical bores or apertures 60 and 62 are defined by generally cylindrical walls 64 and 66, respectively. Note that the bores or apertures 60 and 62 and their respective bore axes A1 and A2, respectively, are angled in different directions (i.e., one upward and one downward in the illustration shown in FIG. 3) so that the screws 50 and 52 may engage and be screwed into different bones, such as the first vertebra or bone 17 and the second vertebra or bone 19.

In the illustration being described, the first wall 12a comprises a first side wall surface 12a1 and a second side wall surface 12a2 that is generally opposed to the first side wall surface 12a1. Note that the first side wall surface 12a1 is posterior relative to the second side wall surface 12a2 when viewed from a front of the implant assembly 10 after the implant assembly 10 is implanted into the implant receiving area 15.

In one embodiment, each of the plurality of bores or apertures 60 and 62 comprises at least one or a plurality of arms, fingers or latches. For example, the first bore or aperture 60 and the second bore or aperture 62 comprise a first arm 70 and a second arm 72, respectively. For ease of illustration, the at least one or a plurality of arms will be illustrated here as comprising the first arm 70 and the second arm 72 associated with the first bore or aperture 60 and the second bore or aperture 62, respectively, but it should be understood that more or fewer apertures could be provided and more or fewer arms could be used or provided in the apertures 60 and 62. The first and second arms 70 and 72 are operatively associated with and located in the first and second bores or apertures 60 and 62, respectively. In the illustration, each of the first and second arms 70 and 72 are flexible, elastic and/or resilient so that they can be actuated from a normally closed position (illustrated in FIGS. 1-4) to an actuated open position (illustrated in FIG. 5 relative to the first arm 70).

Each of the first and second arms 70 and 72 comprises elongated portions 70a and 72a, free ends or detent ends 70b and 72b and fixed ends or coupling ends 70c and 72c. The first and second arms 70 and 72 have an associated arm axis AA1 (FIGS. 3, 9 and 10) and AA2, respectively, in the illustration being described. In this example, the arm axis, such as arm axis AA1, is not parallel or generally not parallel with respect to an imaginary plane IP (FIG. 10) in which the implant assembly 10 lies and is also generally not parallel to a coronal plane CP (illustrated in FIG. 9). For ease of understanding, the imaginary plane IP (FIG. 10) lies generally midway between a first bone-engaging surface 37 and a generally opposed second bone-engaging surface 39, which is adapted and configured to engage or become associated with the first and second vertebrae or bones 17 and 19, respectively, after the implant assembly 10 is received in the implant receiving area 15. The first and second arms 70 and 72 are not generally parallel to the imaginary plane IP or coronal plane CP as mentioned, and it is important to note that they lie at different angles with respect to each other and with respect to the imaginary plane IP and coronal plane CP, as illustrated by the angles Θ and X (FIG. 9) and angles φ and Y (FIG. 10).

In the illustration being described, the first implant member 12 is machined to define the apertures 60 and 62 and their associated first and second arms 70 and 72, respectively. In the illustration being described, the first and second arms 70 and 72 are defined by at least one or a plurality of cut-out areas 84, 85, 86, 87 and 88 (with only areas 84 and 86 labeled in FIG. 7 with respect to first arm 70 for ease of illustration) in a coupling or intermediate portion 90 of the first wall 12a. In the illustration being described, the second arm 72 comprises the elongated portion 72a that joins the free end or detent end 72b and the coupling or fixed end 72c which couples or joins the second arm 72 to the coupling or intermediate portion 90. For example, the first implant member 12 was machined and cut-out areas 84, 85, 86, 87 and 88 were machined or cut out to define the second aperture 62 and its associated second arm 72, as best illustrated in FIG. 7.

The first arm 70 extends from a first side wall surface 12a1 toward the generally opposing second side wall surface 12a2 as best illustrated in FIGS. 7-10. Likewise, the second arm 72 is configured similarly except that it extends upward and toward the reader (as viewed in FIG. 7) from the first side wall surface 12a1 toward an opening 62a of the aperture 62 as illustrated.

Notice that the second arm 72 has the coupling or fixed end 72c that is coupled to or integrally formed in the coupling or intermediate portion 90 and angles upward in the aperture 62 (as viewed in FIGS. 5, 7 and 8) toward the second side wall surface 12a2. In contrast, note that the first arm 70 has its fixed end 70c coupled to or integral with the coupling or intermediate portion 90 and extends or projects in the aperture 60 and angles downward (as viewed in FIGS. 5, 7 and 8) from the first side wall surface 12a1 toward the second side wall surface 12a2. Thus, it should be appreciated that in this embodiment, the first and second arms 70 and 72 diverge as they extend or project away from the coupling or intermediate portion 90 associated with the first side wall surface 12a1.

Advantageously, each of the first and second arms 70 and 72, therefore, extend from the posterior first side wall surface 12a1 toward the anterior second side wall surface 12a2. Thus, as the first and second arms 70 and 72 extend or project from the coupling or intermediate portion 90, they not only generally diverge from each other, but they also generally diverge, project or extend away from both the imaginary plane IP and the coronal plane CP, as illustrated in FIGS. 9 and 10. It is important to note, however, that their axes, namely axes AA1 and AA2, are generally parallel to their respective bore or aperture axes A1 and A2, respectively. This is best shown in FIG. 3.

As illustrated in the Figures, after the implant assembly 10 is implanted, for example, between the first and second vertebrae or bones 17 and 19 (FIG. 4) in the implant receiving area 15, the first side wall surface 12a1 becomes situated posterior relative to the second side wall surface 12a2. Each of the first and second arms 70 and 72 are located in the apertures 60 and 62 and extend or project in the apertures 60 and 62 toward the second side wall surface 12a2 as mentioned, and their respective free ends or detent ends 70b, 72b become operatively positioned and associated with openings 60a and 62a into the apertures 60 and 62, respectively.

Thus, it should be appreciated that the fixed ends 70c and 72c of the first and second arms 70 and 72 are integral with or coupled to the coupling or intermediate portion 90 and extend interiorly in the at least one or a plurality of apertures 60 and 62, respectively, as shown. In the illustration being described, this configuration causes the free end or detent end 70b, 72b of the first and second arms 70 and 72, respectively, to be operatively positioned relative to the entry opening, such as openings 60a and 62a, into the at least one or plurality of apertures 60 and 62. It should be understood that this design is advantageous because it maximizes use of available space by placing the first and second arms 70 and 72 inside the apertures 60 and 62, respectively, as opposed to outside the aperture (such as on the second side wall surface 12a2).

As best illustrated in FIGS. 4-6, after the implant assembly 10 is implanted in the implant receiving area 15, a screw, such as screw 50 or screw 52, can be inserted or received in the apertures 60, 62, respectively, and ultimately screwed into the bones 17 and 19, respectively. Note that the free ends or detent ends 70b and 72b are engaged by the screw heads 50a and 52a, respectively, and are actuated or driven away from their respective axes A1 and A2. For example, when screw head 50a engages the free end or detent end 70b, it is driven or moves in the direction of arrow A in FIG. 5 in response to the axial movement of the screw 50 as it is screwed into the first vertebra or bone 17 (FIGS. 4 and 5).

Figure 2:
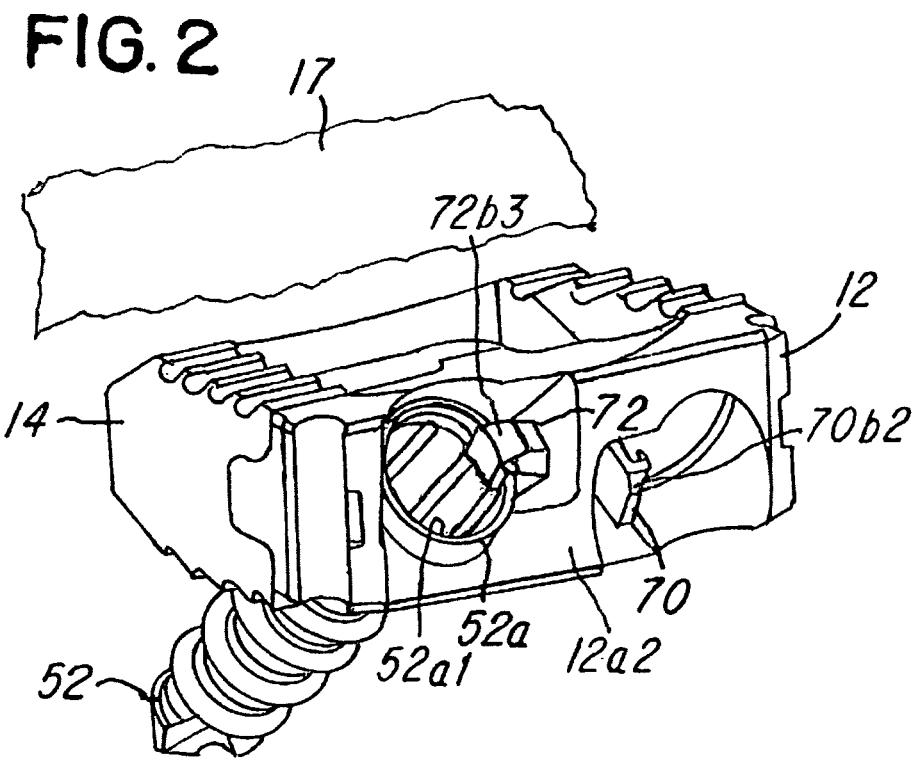
FIG. 2 is another perspective view of the implant shown in FIG. 1.

Each free end or detent end 70b and 72b comprises a generally U-shaped detent 70b1 (FIGS. 4, 6A and 11) and 72b1, respectively. Although the generally U-shaped detent 70b1 and 72b1 are shown situated at the free ends or detent ends 70b and 72b, it should be understood that they could be positioned at other positions or locations on the first and second arms 70 and 72, respectively. The detents 70b1 and 72b1 define receiving areas or locking channels 70b1i and 72b1i, respectively, and each comprise or define a pawl or latch 70d, 72d as best illustrated in FIG. 7. As the screws 50 and 52 are driven axially into the apertures 60 and 62, respectively, when the screws 50 and 52 are screwed into the first vertebra or bone 17 (FIG. 4) and the second vertebra or bone 19, the first and second arms 70 and 72 move or deflect until latches 70d and 72d clear top edges 50a1i and 52a1i of the generally circular wall portions 50a1 and 52a1 (FIG. 1) of the screws 50 and 52, respectively, whereupon the resilient first and second arms 70 and 72 cause the detents 70b1 and 72b1 move back toward their home position toward the axes A1 and A2 of the apertures 60 and 62, respectively. For example, the detent 70b1 moves in the direction of arrow B in FIG. 6 toward the axis A1. This causes the latches 70d and 72d to become operatively positioned so that the receiving areas or locking channels 70b1i and 72b1i, respectively, become generally aligned with, and adapted to receive, the generally circular wall portions 50a1 and 52a1, respectively, as shown in FIGS. 1 and 2.

After the detents 70b1 and 72b1 "clear" the wall portions 50a1 and 52a1, the screws 50 and 52 may be backed out or unscrewed slightly until the top surfaces 50a1i and 52a1i engage the surface 70d1 (FIG. 4) and 72d1, respectively, thereby causing the wall portions 50a1 and 52a1 to be captured in the channels 70b1i and 72b1i, respectively. Note that the wall portions 50a1 and 52a1 comprise a thickness that is slightly smaller than a width W (FIG. 6A) of the channels 70b1i and 72b1i. The screws 50 and 52 become locked or retained in the implant assembly 10 so that they cannot withdraw therefrom or from the first and second vertebrae or bones 17 and 19, thereby locking the screws 50 and 52 in the implant assembly 10. If it is desired to remove the screws 50 and 52, the first and second arms 70 and 72 can be manually deflected to the open position (e.g., first arm 70 can be actuated in the direction of arrow A in FIG. 5) and the screws 50 and 52 unscrewed from the first and second vertebrae or bones 17 and 19, respectively.

Although not shown, a generally L-shaped detent may be used with the free ends if, for example, the screws 50 and 52 did not have the wall portions 50a1 and 52a1.

Advantageously, the generally U-shaped capturing detents 70b1 and 72b1 are adapted to prevent the screws 50 and 52 from withdrawing from the implant assembly 10. This design also facilitates preventing the first and second arms 70 and 72 from splaying or moving away from their respective axes AA1 and AA2, respectively. Notice in FIG. 4 that overhang wall portions 70b3 and 72b3 of detents 70b1 and 72b1, respectively, are generally arcuate or curved and generally complement or match a shape of an inner curved surface 50c and 52c of the screws 50 and 52, as shown in FIGS. 1, 2 and 4-6.

In the illustration being described, the detent 70b1 is defined by and located on the free end or detent end 70b and detent 72b1 is defined by and located on the free end or detent end 72b. As described, the detents 70b1 and 72b1 are generally U-shaped as shown in FIG. 6A, but it should be understood that they could assume other shapes or configurations. As mentioned earlier, each of the first and second arms 70, 72 are defined by machining the first wall 12a of the first implant member 12 as mentioned. The free ends or detent ends 70b, 72b and their respective detents 70b1 and 72b1 are also defined by machining. The detents 70b1 and 72b1 comprise beveled surfaces 70b2 (FIGS. 1, 2 and 4) and 72b2, respectively, that are generally coplanar with the second side wall surface 12a2.

The free ends or detent ends 70b and 72b also comprise generally curved or arcuate camming surfaces 70b3 and 72b3 (FIGS. 1, 2 and 7) which engage the screw heads 50a and 52a, respectively, when the screws 50 and 52 are driven axially into the apertures 60 and 62 as described earlier. The screws 50 and 52 cam against the surfaces 70b3 and 72b4, respectively, which causes the free ends or detent ends 70b and 72b to deflect away from the axes A1 and A2, respectively. Again, it should be noted that the resilient first and second arms 70, 72 are urged away from their respective bores or apertures 60 and 62 and away from the axes A1 and A2 in response to the axial movement of the screws 50 and 52 in the bores or apertures 60 and 62.

It should be understood that the elongated portion, such as the elongated portion 70a of first arm 70 and elongated portion 72a of second arm 72, are in communication with at least one of the plurality of apertures 60, 62, respectively, and notice that they facilitate defining at least a portion of the boundary of the bores or apertures 60, 62, respectively. For example, note relative to the first arm 70 in FIG. 7, the surface 71 facilitates defining a portion or boundary of the bore or aperture 60.

As shown in FIG. 7, walls 64 and 66 comprise seats 64a and 66a, respectively. The seats 64a and 66a are adapted to receive and support the heads 50a and 52a of the screws 50 and 52, respectively, after the screws 50 and 52 are screwed into bone.

Although the embodiment being described shows a pair of apertures, namely apertures 60 and 62, it should be appreciated that more or fewer apertures could be used. Also, it should be understood that the locking system 49 of the embodiments shown and described could be used with other types of implants, such as plates, cages, spinal implants, bone implants, fusion devices and the like.

Referring back to FIG. 7, note that the coupling or intermediate portion 90 is an integral construction in the first wall 12a and it integrally joins and couples the fixed ends or coupling ends 70c and 72c as shown. The coupling or intermediate portion 90 is situated between the first and second arms 70 and 72 and facilitates and enables the first and second arms 70 and 72 to extend from the first side wall surface 12a1 toward the second side wall surface 12a2 so that the first and second arms 70 and 72 can extend or project into the apertures 60 and 62, respectively. This configuration also enables the free ends or detent ends 70b and 72b to become operatively associated with openings 60a and 62a, respectively, into the apertures 60 and 62 as mentioned earlier. Advantageously, the coupling or intermediate portion 90 is generally situated or located between the pair of apertures 60 and 62 as shown.

As illustrated in FIGS. 9 and 10, the first and second side wall surfaces 12a1 and 12a2 are generally perpendicular to the imaginary plane IP and generally parallel to the coronal plane CP. As mentioned earlier herein, the axes AA1 and AA2 of the first and second arms 70 and 72 diverge (as illustrated in FIGS. 7, 9 and 10), and they are generally not parallel to either the imaginary plane IP or the coronal plane CP. Indeed and as mentioned earlier herein, the axes AA1 and AA2 of the first and second arms 70 and 72 form acute angles $\Theta$, $\phi$ and X, Y, respectively, of generally less than about 45 degrees with respect to the imaginary plane IP and coronal plane CP. In a preferred embodiment the angles $\Theta$ and $\phi$ are between about 20-70 degrees and angles X and Y are between about 20-70 degrees. For example, note that the angles Θ and X in FIG. 9, which shows the angles between the imaginary plane IP and the coronal plane CP and the longitudinal axis AA1 of the first arm 70, is less than about 45 and 70 degrees, respectively. Again, and as mentioned earlier herein, this axis AA1 and the imaginary plane IP and the coronal plane CP are generally not parallel, but axis AA1 and axis A1 of the aperture 60 are generally parallel. Likewise, and as shown in FIG. 10, the axis AA2 is not generally parallel to the imaginary plane IP and the coronal plane CP, but it is generally parallel to the axis A2, which is the axis of the aperture 62.

The free ends or detent ends 70b and 72b extend between the first and second side wall surfaces 12a1 and 12a2 as shown. Indeed, a majority, if not all, of the first and second arms 70 and 72, including their respective elongated portions 70a and 72a, are in communication with and lie in and project or extend a substantial or majority of a length of the apertures 60 and 62. After the screws 50 and 52 are received in the apertures 60 and 62, note that their axes become generally co-axial with the axes A1 and A2, respectively, of apertures 60 and 62. The axes of the screws 50 and 52 also become generally parallel to the axes AA1 and AA2, respectively, of the first and second arms 70 and 72.

Advantageously, the configuration of the screw locking system 49 described herein associates the fixed end or coupling end 70c and 72c with exit areas 60b and 62b, respectively, of the apertures 60 and 62 and the free ends or detent ends 70b and 72b with the openings 60a and 62a into the apertures 60 and 62.

During use, the first and second implant members 12 and 14 are assembled by sliding the projection 18 into the channel 22. The generally U-shaped projection 18 is guided into the channel 22 until the holes or bores 40 and 42 become generally aligned with the holes or bores 28, 34 and 30, 36, respectively. Once they become aligned, the pins 44 and 46, can be inserted as illustrated in FIGS. 7-10, and the first implant member 12 and second implant member 14 become locked together to provide the implant assembly 10. The generally U-shaped projection 18 cooperates with the first wall 12a to define a fusion material receiving area 73 (FIG. 3). This fusion material receiving area 73 is filled with a fusion or graft material by the user. The implant assembly 10 is situated between the first and second vertebrae or bones 17 and 19 in the implant receiving area 15 as generally illustrated in FIG. 4. In this assembled position, the surface 18a of the projection 18 becomes generally coplanar with the generally U-shaped third wall portion 20c as shown in FIG. 7.

After the implant assembly 10 is positioned in the implant receiving area 15, the screws 50 and 52 are guided into the apertures 60, 62, respectively, and screwed into the first and second vertebrae or bones 17 and 19 until the channels 70b1i and 72b1i become operatively associated with and positioned generally opposed to the wall portions 50a1 and 52a1, respectively, as described earlier herein. As mentioned earlier, after the screws 50 and 52 "clear" their respective detents 70b, 72b, the first and second arms 70, 72 urge the detents 70b, 72b to their home position, whereupon the channels 70b1i and 72b1i become operatively associated or positioned in opposed relationship to the wall portions 50a1 and 52a1, respectively. The user may optionally unscrew or back out the screws 50 and 52 enough to cause the wall portions 50a1 and 52a1 to be captured in their respective generally U-shaped channel 70b1i or 72b1i. The implant assembly 10 becomes screwed and locked in the implant receiving area 15, thereby preventing the first implant member 12 separating from the second implant member 14, facilitating preventing the screws 50 and 52 from unscrewing, and also preventing the implant assembly 10 from expulsion or withdrawing from the implant receiving area 15 once the screws 50 and 52 are locked in the apertures 60 and 62 by the detents 70b1 and 72b1, respectively. If the screws 50 and 52 expel or unscrew, the wall portions 50a1 and 52a1 will be captured in the channels 70b1i and 72b1i, respectively.

Advantageously, the implant assembly 10 comprises the screw locking system 49 which facilitates preventing at least one or a plurality of screws, such as screws 50 and 52, from withdrawing from the implant assembly 10. Although the apertures 60 and 62 and their associated first and second arms 70 and 72, respectively, are shown as extending in diverging directions as described earlier, it should be understood that the apertures 60, 62 and the first and second arms 70, 72 could be arranged differently. For example, they could be arranged so that the axes AA1 and AA2 are generally parallel, extend in the same direction but diverge or converge in a common horizontal or vertical plane, extend in different directions and diverge, as illustrated in FIGS. 1-10, but with angles Θ, X (FIG. 9) and ϕ, Y (FIG. 10) that are different, or the like. An important feature, however, is that the at least one or a plurality of the apertures have the screw locking system 49 in the form of at least one or a plurality of arms, such as one or more of the first and second arms 70, 72, respectively, and the arm axes, such as the axes AA1 and AA2 of the first and second arms 70 and 72, respectively, are generally parallel with the aperture axes, such as the axes A1 and A2 of the apertures 60 and 62. Note that a majority of the first and second arms 70 and 72, including the elongated portions 70a, 72a, are situated in the apertures 60 and 62, respectively.

Another feature is that the first and second arms 70, 72 are situated in the apertures which is advantageous because of space and size constraints associated with the second side wall surface 12a2. Situating a majority or all of the first and second arms 70, 72 in the apertures 60, 62, respectively, enables the use of the first and second arms 70 and 72.

In one embodiment, the first and second implant members 12 and 14 are made of different materials, such as PEEK and titanium, with the second implant member 14 having a modulus of elasticity similar to bone.

FIG. 12 shows another embodiment wherein the implant assembly 10″ is an integral, one-piece body 17″ construction, rather than the two-piece construction shown in FIG. 1. In this embodiment, like parts are identified with the same part numbers, except that a double prime mark ("″") has been added to the part numbers. In one embodiment, the implant assembly 10″ is a monolithic construction machined from titanium. Notice it has the locking system 49″ the same or similar to the embodiment of FIGS. 1-11.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. An implant comprising:
an implant member adapted to be received in an implant receiving area between a first bone and a second bone, said implant member comprising a first wall containing at least one or a plurality of apertures wherein each of the at least one or a plurality of apertures are adapted to receive one screw having a screw body comprising a screw head and a threaded portion, wherein a top surface of the screw head extends transverse to a longitudinal axis of said threaded portion of the screw, said implant member having a first bone-engaging surface and a second bone-engaging surface opposite to the first bone-engaging surface having an imaginary plane lying midway between said first bone-engaging surface and said second bone-engaging surface;

said first wall of said implant member comprising at least one or the plurality of arms extending from said first wall, and wherein each of said at least one or a plurality of arms comprises a detent comprising an inner surface, wherein the inner surface associated with said top surface of said one screw head after said one screw is received in each aperture of said at least one or the plurality of apertures, said detent being adapted to retain said one screw in each aperture of said at least one or the plurality of apertures, wherein each arm of said at least one or the plurality of arms comprises a generally elongated portion, the generally elongated portion defining an arm axis, each arm of said at least one or the plurality of arms being flexible, resilient or elastic, and wherein each aperture of said at least one or the plurality of apertures comprises an aperture axis parallel to a longitudinal axis of said one screw received in the each aperture said at least one or the plurality apertures, said arm axis of each arm of said at least one or the plurality of arms being generally parallel to said longitudinal axis of a screw received in the aperture.

2. The implant as recited in claim 1, wherein said generally elongated portion of each arm of said at least one or the plurality of arms extends in each aperture of said at least one or said plurality of apertures.

3. The implant as recited in claim 1, wherein said implant member comprises a first wall having a first side wall surface and a generally opposing second side wall surface, said first side wall surface being posterior to said second side wall surface after said implant is implanted, each of said at least one or the plurality of apertures extending through said first and second side wall surfaces of said first wall and each of said at least one or the plurality of arms having a first end proximate to said first side wall surface and being coupled to or integral with said implant member, an arm of said at least one or the plurality of arms being located in each of said at least one or the plurality of apertures and extending in each of said at least one or the plurality of apertures toward said second side wall surface.

4. The implant as recited in claim 3, wherein said first wall of said implant member comprises a first implant member and a second implant member, said first implant member having a generally U-shaped projection that projects from said first wall, said generally U-shaped projection cooperating with said first wall and defining a receiving area.

5. The implant as recited in claim 1, wherein said arm axis intersects said imaginary plane at a predetermined angle.

6. The implant as recited in claim 1, wherein each of said at least one or the plurality of arms defines a resilient finger having an end integrally formed in or coupled to said implant member, said resilient finger being urged away from each of said at least one or the plurality of apertures in response to axial movement of said screw into each of said at least one or the plurality of apertures.

7. The implant as recited in claim 6, wherein at least a portion of said resilient finger becomes operatively associated with said screw head after said screw is received in each of said at least one or said plurality of apertures, thereby facilitating preventing said screw from withdrawing from said implant.

8. The implant as recited in claim 6, wherein said resilient finger is normally biased such that said detent is in a screw-locking position.

9. The implant as recited in claim 1, wherein said implant member comprises said at least one or the plurality of apertures, wherein each said at least one or the plurality of arms is associated with each of said at least one or the plurality of apertures, wherein said at least one or the plurality of arms having a detent adapted to retain said screw in said implant member after said screw has been received in at least one of said at least one or the plurality of apertures.

10. The implant as recited in claim 9, wherein said first side wall surface is generally opposing second side wall surface, said first side wall surface being posterior to said second side wall surface after said implant is implanted, each of said at least one or the plurality of apertures extending through said first and second side wall surfaces of said first wall, each of said at least one or the plurality of arms having a first end proximate to said first side wall surface, wherein the generally elongated portion extends in each of said at least one or the plurality of apertures toward said second side wall surface.

11. The implant as recited in claim 9, wherein said first side wall surface is generally opposing second side wall surface, said first and second side wall surfaces, each of said at least one or the plurality of arms being configured to extend substantially between said first and second side wall surfaces.

12. The implant as recited in claim 9, wherein each of said at least one or the plurality of apertures comprises a first end for inserting said screw and a second end associated with said first or second bone engaging surface, said at least one or the plurality of arms having a free end associated with said first end, a fixed end associated with said second end, and said generally elongated portion joining said free end and said fixed end, at least a portion of said generally elongated portion lying in said each aperture of said at least one or said plurality of apertures between said first end and said second end.

13. The implant as recited in claim 12, wherein each of said generally elongated portions is located in said each aperture of said at least one or said plurality of apertures.

14. The implant as recited in claim 9, wherein each of said at least one or the plurality of arms is defined by a cut-out in said implant member.

15. The implant as recited in claim 9, wherein said implant further comprises a second implant member adapted to be received between bones and having an open end configured to receive said implant member.

16. The implant as recited in claim 15, wherein said second implant member is generally U-shaped and comprises a generally U-shaped channel, said implant member comprises an implant member generally U-shaped projection portion that defines a receiving area adapted to receive a material for fusing adjacent bones together, said implant member generally U-shaped projection being adapted to be slidably received in said generally U-shaped channel.

17. The implant as recited in claim 16, wherein said implant comprises a lock for locking said implant member and said second implant member together.

18. The implant as recited in claim 17, wherein said lock comprises a pin, said implant member and said second implant member each comprising at least one or the plurality of apertures that becomes generally aligned after said implant member is received in said implant member.

19. The implant as recited in claim 9, wherein said implant comprises a plurality of walls, each of said plurality of walls define said at least one or the plurality of apertures, with each said at least one or the plurality of arms being located in each of said at least one or the plurality of apertures, each wall of said plurality of walls defining a first end opening where said screw is introduced into each said at least one or the plurality of apertures and a second end opening wherein said screw exits each said at least one or the plurality of apertures, each arm of said at least one or the plurality of arms extending between a second end of each aperture of said at least one or the plurality of apertures and a first end of each aperture of said at least one or the plurality of apertures, said detent being biased in operative relationship to said screw head in order to retain said screw head in said implant member after said screw has been inserted into each aperture of said at least one or the plurality of apertures and screwed into bone.

20. The implant as recited in claim 9, wherein said detent flexed to an open position in response to axial movement of at least one screw being inserted therein.

21. The implant as recited in claim 9, wherein said generally elongated portion of each of said at least one or the plurality of arms is in communication with each of said at least one or the plurality of apertures.

22. The implant as recited in claim 1, wherein said at least one or a plurality of arms comprises two arms that diverge away from each other as they project from an attachment area to said implant member where said two arms are attached to said implant member by either a coupling or are integrally with said implant member.

23. The implant as recited in claim 22, wherein the at least one or the plurality of apertures comprise two apertures, said attachment area of each arm of the two arms being situated between each aperture of said two apertures.

24. The implant as recited in claim 22, wherein said first side wall surface is generally opposing second side wall surface, said first side wall surface being posterior to said second side wall surface after said implant member is implanted, each of said at least one or the plurality of apertures extending through said first wall and said second side wall surfaces of said first wall and said coupling area being associated with said first side wall surface.

25. The implant as recited in claim 1, wherein each of said at least one or the plurality of apertures traversing through said first and second side wall surfaces, and wherein each of said at least one or the plurality of arms being configured to extend substantially between said first and second side wall surfaces at a predetermined angle.

26. The implant as recited in claim 1, wherein each said at least one or the plurality of apertures comprises a first end for receiving a screw and a second end associated with said first or second bone-engaging surfaces, said at least one or the plurality of arms having a free end associated with said first end, a fixed end associated with said second end, and said generally elongated portion joining said free end and said fixed end, at least a portion of said generally elongated portion lying in at least one or the plurality of apertures between said first end and said second end.

27. The implant as recited in claim 1, wherein said detent prevents said screw from withdrawing from said at least one or the plurality of apertures after said implant is implanted.

28. The implant as recited in claim 1, wherein said detent is generally U-shaped.

29. The implant as recited in claim 1, wherein said detent is generally U-shaped and part of an end of each of said at least one or the plurality of arms.

30. The implant as recited in claim 1, wherein said each arm of said at least one or the plurality of arms and said detent are integral and defined by a cut-out in said implant member.

31. The implant as recited in claim 1 wherein said implant member is an integral one-piece construction.

32. The implant as recited in claim 1, wherein said implant further comprises a first implant member and a second implant member, both of which are adapted to be received between bones, said second implant member having an open end configured to receive said first implant member and mate with said first implant member.

33. The implant as recited in claim 32, wherein said implant comprises a lock for locking said implant member and said second implant member together to prevent relative movement of said implant member and said second implant member.

34. The implant as recited in claim 33, wherein said lock comprises a pin.

35. The implant as recited in claim 32, wherein said at least one of said second implant member comprises a guide channel, and said first implant member comprising a projection that is received in said guide channel.

36. The implant as recited in claim 35, wherein said guide channel is a generally U-shaped channel, said projection defining a generally U-shaped projection adapted to mate with and be received in said generally U-shaped channel.

37. The implant as recited in claim 35, wherein
at least one of said first wall or said second wall comprising a plurality of wall bores;
said projection having a plurality of projection apertures that becomes generally aligned with and in communication with each said plurality of wall bores to define a locking aperture for receiving a lock.

38. The implant as recited in claim 37, wherein said lock is a pin.

39. The implant as recited in claim 32, wherein said second implant member has a general U-shape and open end configuration and comprises a generally U-shaped channel and said first implant member comprises a generally U-shaped projection that is adapted to mate with and be received in said generally U-shaped channel.

40. The implant of claim 1, wherein said generally elongated portion of said arm is coplanar to a screw axis.

41. An implant comprising:
a first implant member comprising at least one or a plurality of apertures each aperture of said at least one or the plurality of apertures adapted to receive a screw having a screw body comprising a screw head, and a threaded portion, wherein a top surface of the screw head extends transverse to a longitudinal axis of said threaded portion of the screw, said first implant member having a first bone-engaging surface and a second bone-engaging surface opposite the first bone-engaging surface, and an imaginary plane lying midway between said first bone-engaging surface and said second bone-engaging surface;
a second implant member adapted to be received between bones, said second implant member having an opening to receive and mate with said first implant member;
said first implant member comprising at least one or a plurality of arms, each arm extending between said first and second bone-engaging surfaces, each arm of said at least one said plurality of arms associated with each aperture of said at least one of said plurality of apertures, in said first implant member, said each arm of said at least one or said plurality of arms being adapted to retain a screw in said each aperture of said at least one or said plurality of apertures, respectively, after said screw have been received in said each aperture of said at least one or said plurality of apertures, wherein at least a portion of said each arm of said at least one or said plurality of arms engages with said top surface of said screw;

said each aperture of said at least one or said plurality of apertures having an aperture axis for receiving said screw, said arm axis of said at least one or said plurality of arms being generally parallel to said aperture axis; and said each arm of said at least one or said plurality of arms being flexible, resilient or elastic and each arm having a generally elongated portion having an arm axis, wherein the arm axis is coplanar to said aperture axis;

wherein said first implant member comprises a plurality of walls, each wall of said plurality of walls define said at least one or said plurality of apertures, respectively, said each aperture of said at least one or said plurality of apertures having an aperture axis and at least one arm of said at least one or said plurality of arms associated therewith, said arm axis of said generally elongated portion being generally parallel to said aperture axis.

42. The implant as recited in claim 41, wherein said generally elongated portion arm is in communication with at least one aperture of said at least one or said plurality of apertures.

43. The implant as recited in claim 41, wherein said plurality of arms diverge as they project or extend away from a coupling area of said first implant member wherein said at least one or said plurality of arms are coupled to or integral with said first implant member.

44. The implant as recited in claim 43, wherein said at least one or said plurality of apertures comprises at least one pair of apertures, said coupling area being situated between said at least one pair of apertures.

45. The implant as recited in claim 43, wherein said first implant member comprises a first wall having a first side wall surface and a generally opposing second side wall surface, said first side wall surface being posterior to said second side wall surface after said first implant member is implanted, said at least one or said plurality of apertures extending through said first and second side wall surfaces of said first wall and said coupling area being associated with said first side wall surface.

46. The implant as recited in claim 41, wherein said first implant member comprises a first wall having a first side wall surface and a generally opposing second side wall surface, said first side wall surface being posterior to said second side wall surface after said first implant member is implanted, said at least one or said plurality of apertures extending through said first and second side wall surfaces of said first wall, said each arm of said at least one or said plurality of arms having a first end proximate to said first side wall surface and said generally elongated portion such that said arm of said at least one or said plurality of arms extends or projects in said each aperture of said at least one or said plurality of apertures toward said second side wall surface.

47. The implant as recited in claim 41, wherein said first implant member comprises a first wall having a first side wall surface and a generally opposing second side wall surface, said first and second side wall surfaces being generally perpendicular to said imaginary implant plane, each arm of said at least one or said plurality of arms being configured to extend substantially between said first and second side wall surfaces such that their longitudinal axis is situated at a predetermined angle relative to said imaginary implant plane of said first implant member.

48. The implant as recited in claim 41, wherein said arm axis intersects said imaginary plane at a predetermined angle.

49. The implant as recited in claim 41, wherein each arm of said at least one or said plurality of arms has a fixed end, and a detent comprising an inner surface that becomes operatively associated with said screw head to facilitate preventing said screw from withdrawing from said each aperture of said at least one or said plurality of apertures.

50. The implant as recited in claim 49, wherein said detent is generally U-shaped.

51. The implant as recited in claim 41, wherein each arm of said at least one or said plurality of arms are defined by at least one cut-out in said first implant member.

52. The implant as recited in claim 41, wherein said second implant member is generally U-shaped and comprises a guide channel, said second implant member comprises a second implant member generally U-shaped projection portion that defines a receiving area adapted to receive a material for fusing adjacent bones together, said second implant member generally U-shaped projection being adapted to be slidably received in said guide channel.

53. The implant as recited in claim 52, wherein said implant comprises a lock for locking said first implant member and said second implant member together.

54. The implant as recited in claim 53, wherein said lock comprises a pin, said first implant member and said second implant member each comprising a plurality of bores that become generally aligned to define a lock aperture after said second implant member is received in said first implant member, said lock aperture being configured to receive said pin.

55. The implant as recited in claim 41, wherein said second implant member comprises a guide channel and said second implant member comprises a projection configured to be received in said guide channel, said projection being adapted to define a graft receiving area for receiving graft material.

56. The implant as recited in claim 55, wherein
at least one of said first wall or said second wall comprising a plurality of wall bores;
said projection having a plurality of projection apertures that becomes generally aligned with and in communication with said plurality of wall apertures to define a locking aperture for receiving a lock.

57. The implant as recited in claim 56, wherein said lock is a pin.

58. The implant of claim 41, wherein each of said generally elongated portions is located in said each aperture of said at least one or said plurality of apertures.

59. An implant comprising:
an implant body adapted to be received in an implant receiving area between a first bone and a second bone, said implant body comprising at least one or a plurality of apertures, each aperture adapted to receive one screw having a screw body comprising a screw head and a threaded portion, wherein a top surface of the screw head extends transverse to a longitudinal axis of said threaded portion of the screw, the screw head defining a locking wall, said implant body having a first bone-engaging surface and a second bone-engaging surface opposite the first bone-engaging surface having an imaginary plane lying midway between said first and said second bone-engaging surfaces;

said implant body comprising at least one or a plurality of resilient, elastic or flexible arms, each arm having a detent comprising an inner surface, wherein the inner surface is associated with said top surface of said screw head after said one screw is received in each of said at least one or said plurality of apertures, said detent being adapted to capture at least a portion of said locking wall of said screw, thereby locking or retaining said screw in said implant;

each of said at least one or said plurality of resilient, elastic or flexible arms having a generally elongated portion having an arm axis; and said at least one or said plurality of apertures having an aperture axis for receiving said screw, said arm axis of said generally elongated portion being generally coplanar to said aperture axis.

60. The implant as recited in claim 59, wherein said detent that has a detent wall that defines a channel for capturing said at least a portion of said locking wall of said screw.

61. The implant as recited in claim 59, wherein said detent comprises a generally U-shaped portion.

62. The implant of claim 59, wherein each of said generally elongated portions is located in said each aperture of said at least one or said plurality of apertures.

* * * * *